(12) United States Patent
Kai

(10) Patent No.: US 6,999,890 B2
(45) Date of Patent: Feb. 14, 2006

(54) MEASUREMENT DATA PROCESSING SYSTEM

(75) Inventor: Akinori Kai, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 0 days.

(21) Appl. No.: 10/276,815

(22) PCT Filed: May 15, 2001

(86) PCT No.: PCT/JP01/04056

§ 371 (c)(1),
(2), (4) Date: Nov. 15, 2002

(87) PCT Pub. No.: WO01/88764

PCT Pub. Date: Nov. 22, 2001

(65) Prior Publication Data

US 2003/0158693 A1    Aug. 21, 2003

(30) Foreign Application Priority Data

May 16, 2000 (JP) ............................. 2000-143895

(51) Int. Cl.
G06F 19/00 (2006.01)
(52) U.S. Cl. .............. 702/122; 702/188; 340/870.05
(58) Field of Classification Search ........... 702/33–36, 702/56, 122, 127, 183–184, 187–188; 340/870.01, 340/870.02, 870.05, 937
See application file for complete search history.

(56) References Cited

U.S. PATENT DOCUMENTS

| | | | | |
|---|---|---|---|---|
| 4,064,455 A | * | 12/1977 | Hopkins et al. | ............. 324/663 |
| 4,697,181 A | * | 9/1987 | Swanson | ............... 340/870.02 |
| 4,752,899 A | * | 6/1988 | Newman et al. | ............ 702/188 |
| 4,862,493 A | * | 8/1989 | Venkataraman et al. | ....................... 379/106.04 |
| 5,136,285 A | * | 8/1992 | Okuyama | .............. 340/870.11 |
| 5,353,238 A | * | 10/1994 | Neef et al. | .................. 702/184 |
| 5,511,422 A | * | 4/1996 | Hernandez | .................... 73/593 |
| 5,539,396 A | * | 7/1996 | Mori et al. | ............ 340/870.01 |
| 5,541,840 A | * | 7/1996 | Gurne et al. | .................. 701/33 |
| RE35,793 E | * | 5/1998 | Halpern | ....................... 702/62 |
| 5,852,351 A | * | 12/1998 | Canada et al. | .............. 318/490 |
| 5,854,994 A | * | 12/1998 | Canada et al. | ................ 702/56 |
| 5,892,758 A | * | 4/1999 | Argyroudis | ................. 370/335 |
| 5,907,491 A | * | 5/1999 | Canada et al. | ............. 700/108 |
| 5,922,963 A | * | 7/1999 | Piety et al. | ..................... 73/659 |
| 5,956,658 A | * | 9/1999 | McMahon | ................... 702/83 |
| 5,991,707 A | * | 11/1999 | Searles et al. | ............. 702/185 |
| 6,128,583 A | * | 10/2000 | Dowling | ...................... 702/58 |

(Continued)

FOREIGN PATENT DOCUMENTS

JP       7-141401       6/1995

(Continued)

*Primary Examiner*—Marc S. Hoff
*Assistant Examiner*—Mary Catherine Baran
(74) *Attorney, Agent, or Firm*—Hamre, Schumann, Mueller & Larson, P.C.

(57) ABSTRACT

A measurement data processing system is provided, which can transmit measurement data for processing from a data measuring device that has measured and stored the data to a data processing device without a complicated operation. When a personal measuring instrument (1) is connected to a cable (3), followed by turning on a power switch (1*a*) or when a personal measuring instrument (1) whose power switch (1*a*) is on is connected to a computer (2) via a cable (3), the computer (2) automatically executes a series of operations including fetching the measurement data stored in the personal measuring instrument (1), analyzing the data and then outputting the results of processing to a printer (4).

10 Claims, 4 Drawing Sheets

U.S. PATENT DOCUMENTS 6,138,078 A * 10/2000 Canada et al. ................. 702/44
6,216,096 B1 * 4/2001 Obermeier .................. 702/177
6,366,871 B1 * 4/2002 Geva .......................... 702/188

FOREIGN PATENT DOCUMENTS

JP        10-295651      11/1998
JP        2000-132622    5/2000

* cited by examiner

US 6,999,890 B2

MEASUREMENT DATA PROCESSING SYSTEM

TECHNICAL FIELD

The present invention relates to a measurement data processing system including a data measuring device for measuring and storing data of a subject for measurement, and a data processing device for fetching and processing the data stored in the measuring device, wherein various data processings such as compilation, analysis and printing are performed.

BACKGROUND ART

Conventionally, there have been known personal measuring devices that enable patients to measure various data by themselves outside medical facilities (for example, an electrocardiograph, a sphymomanometer, a blood sugar level meter or a urinalysis device). Also known are systems in which data self-measured by patients are stored in a recording medium contained in a personal measuring device and the stored data are read out from the recording medium and analyzed by a personal computer located in a medical facility or the like. With such systems, doctors and the like can carry out medical treatment and give living guidance based on the data self-measured by the patients using the personal measuring device.

In such conventional systems, when analyzing data stored in the personal measuring device, it is necessary to carry out a series of troublesome personal-computer operations including starting-up a personal computer and activating a software for processing the data in advance, and then connecting the personal measuring device of the patient to this personal computer, followed by (1) setting the personal computer in a receive mode for reading out the stored data from the personal measuring device to the personal computer, (2) making the personal measuring device transmit the data to the personal computer, (3) checking if the data is received properly on the personal computer side, (4) processing the data and displaying the result thereof, (5) printing the result and (6) terminating the data processing program.

Further, there also are cases in which a patient need not consult a doctor and just wants to print out the result of data analysis for the purpose of self-management. In such cases, it is favorable if the patient can read out data and print out the result of analysis by him/herself without seeking any assistance of staff members at a medical facility. However, this is practically impossible because, understandably, not every patient who has a personal measuring device is familiar with the operation of a personal computer.

It is an object of the present invention to solve the problems described above and to provide a measurement data processing system that fetches measurement data stored in a personal measuring device to a data processing device and starts processing the data automatically, simply by connecting the personal measuring device to the data processing device such as a personal computer and turning on power or by connecting the personal measuring device whose power has been turned on to the data processing device.

DISCLOSURE OF INVENTION

In order to achieve the above-mentioned object, a first measurement data processing system according to the present invention includes a data measuring device for measuring and storing data, and a data processing device for fetching and processing the data from the data measuring device and then outputting a result of the processing. After the data measuring device is connected to the data processing device, the data processing device starts fetching the data from the data measuring device when triggered by turning on a power of the data measuring device.

In this manner, it is possible to provide a measurement data processing system with which even a user who is unfamiliar with an operation of a computer or the like easily can obtain the processing results of measurement data simply by connecting a data measuring device to a data processing device and turning on power.

In the first measurement data processing system, it is preferable to judge whether the data measuring device is connected to the data processing device when the power is turned on, set an operation mode to be a data transmitting mode if the data measuring device is connected to the data processing device, and set the operation mode to be a data measuring mode if the data measuring device is not connected to the data processing device.

Accordingly, a user of the data measuring device does not have to switch the operation modes, bringing the advantages of saving time for operation and avoiding operation errors.

In the first measurement data processing system, it is preferable that the data processing device automatically executes a series of operations from fetching the data to outputting the result of the processing when triggered by turning on the power of the data measuring device.

In this manner, it is possible to provide a measurement data processing system with which even a completely computer-illiterate user easily can obtain processing results of measurement data simply by connecting a data measuring device and turning on power.

Further, in order to achieve the above-mentioned object, a second measurement data processing system according to the present invention includes a data measuring device for measuring and storing data, and a data processing device for fetching and processing the data from the data measuring device and then outputting a result of the processing. The data processing device starts fetching the data from the data measuring device when triggered by connecting the data measuring device to the data processing device.

With this configuration, it is possible to provide a measurement data processing system with which even a user who is unfamiliar with an operation of a computer or the like easily can obtain processing results of measurement data simply by connecting a data measuring device to a data processing device.

In the second measurement data processing system, it is preferable that the data processing device automatically executes a series of operations from fetching the data to outputting the result of the processing when triggered by connecting the data measuring device to the data processing device. In this manner, even a user who is unfamiliar with an operation of a computer or the like easily can obtain processing results of measurement data simply by connecting a data measuring device.

Also, in the second measurement data processing system, it is preferable that the data measuring device is connected to the data processing device via a public communication network. This allows a user of a data measuring device to transmit measurement data to the data processing device for processing via a public communication network such as a telephone network from a remote location without visiting a place where the data processing device is located.

Furthermore, it is preferable that the result of processing the data is output from the data processing device to a receiver of a user of the data measuring device. This receiver can be a facsimile receiver or a personal computer at the user's house, or a portable terminal such as a cellular phone of the user. This allows the user of the data measuring device to obtain the result of processing the measurement data at home or at any place away from home without visiting a place where the data processing device is located.

Moreover, in order to achieve the above-mentioned object, a first data measuring device according to the present invention is a data measuring device for measuring and storing data and transmitting the data to a data processing device. The data measuring device includes an interface portion for judging whether the data measuring device is connected to the data processing device when a power is turned on, and an operation controlling portion for setting an operation mode to be a data transmitting mode if the data measuring device is connected to the data processing device, and setting the operation mode to be a data measuring mode if the data measuring device is not connected to the data processing device.

Further, a second data measuring device is a data measuring device for measuring and storing data and transmitting the data to a data processing device. The data measuring device includes an interface portion for judging whether the data measuring device is connected to the data processing device, and an operation controlling portion for setting an operation mode to be a data transmitting mode when the interface portion detects that the data measuring device is connected to the data processing device, and setting the operation mode to be a data measuring mode if the data measuring device is not connected to the data processing device.

With these configurations, it is possible to provide a data measuring device that can transmit data to a data processing device even if a user does not carry out a complicated operation such as switching of operation modes.

Also, in order to achieve the above-mentioned object, a first data processing device according to the present invention is a data processing device for receiving and processing data from a data measuring device that has measured and stored the data. The data processing device includes an interface portion that receives a predetermined signal from the data measuring device after the data measuring device is connected to the data processing device, thereby detecting that the power of the data measuring device is turned on, and a data processing portion that starts fetching the data from the data measuring device when triggered by detecting that the power of the data measuring device is turned on.

Further, a second data processing device according to the present invention is a data processing device for receiving and processing data from a data measuring device that has measured and stored the data. The data processing device includes an interface portion that receives a predetermined signal from the data measuring device, thereby detecting that the data measuring device is connected to the data processing device, and a data processing portion that starts fetching the data from the data measuring device when triggered by connecting the data measuring device to the data processing device.

With these configurations, it is possible to provide a data processing device with which even a user who is unfamiliar with an operation of a computer or the like easily can obtain processing results of measurement data simply by connecting a data measuring device and turning on power.

Furthermore, a first program recording medium according the present invention stores a program for allowing a computer to execute operations of, after a data measuring device that has measured and stored data is connected to the computer, receiving a predetermined signal from the data measuring device, thereby detecting that the power of the data measuring device is turned on, starting fetching the data from the data measuring device when triggered by detecting that the power of the data measuring device is turned on, processing the data that have been fetched, and outputting a result of the processing.

In addition, a second program recording medium according the present invention stores a program for allowing a computer to execute operations of receiving a predetermined signal from a data measuring device, thereby detecting that the data measuring device that has measured and stored data is connected to the computer, starting fetching the data from the data measuring device when triggered by connecting the data measuring device to the computer, processing the data that have been fetched, and outputting a result of the processing.

A computer is made to read out a program from these recording media, whereby it is possible to achieve a system with which even a user who is unfamiliar with a computer operation easily can obtain computer-processed results of measurement data simply by connecting a data measuring device to a computer and turning on power.

BEST MODE FOR CARRYING OUT THE INVENTION

The following is a description of an embodiment of the present invention, with reference to the accompanying drawings.

Figure 1:
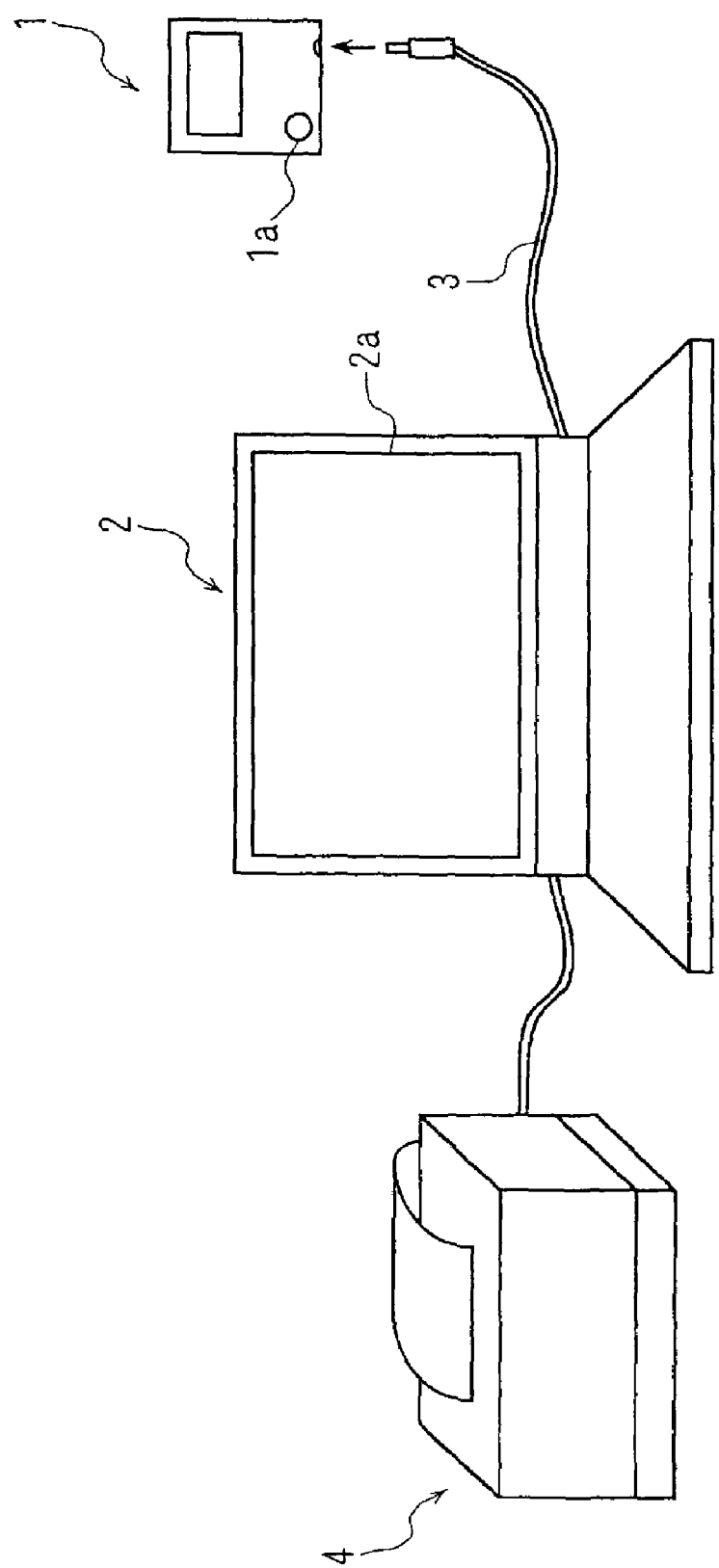
FIG. 1 shows a schematic configuration of a measurement data processing system according to an embodiment of the present invention.

FIG. 1 shows a schematic configuration of a measurement data processing system according to the present embodiment. This data processing system includes a personal measuring instrument 1, a computer 2 serving as a data processing device that reads out data from the personal measuring instrument 1 and performs compilation, analysis and the like, a cable 3 for connecting the personal measuring instrument 1 and the computer 2 at the time of reading out the data, and optionally, a printer 4 for printing out the results of data processing in the computer 2, and other peripheral equipment.

The personal measuring instrument 1 is owned by a patient and used for self-measurement of data outside a medical facility. In the present embodiment, the personal measuring instrument 1 performs measurement in a state disconnected from the computer 2 (an off-line state), and the measured data are stored in a recording medium (described later) contained in this personal measuring instrument 1. The computer 2 and the printer 4 are located at the medical facility. A user of the personal measuring instrument 1 brings the personal measuring instrument 1 to this medical facility and connects the personal measuring instrument 1 to the computer 2 so that the stored data are read out. The computer 2 analyzes the data read out from the personal measuring instrument 1 and displays results of this processing on a display 2a of the computer 2 and/or outputs the results to the printer 4 for printing.

In this data processing system, a series of operations from reading out the data from the personal measuring instrument 1 into the computer 2 to outputting the analysis results is executed by a very simple operation of connecting the personal measuring instrument 1 to the computer 2 via the cable 3 and then turning on a power switch 1a.

In the following, a configuration and an operation of each portion in this data processing system will be described more specifically.

Figure 2:
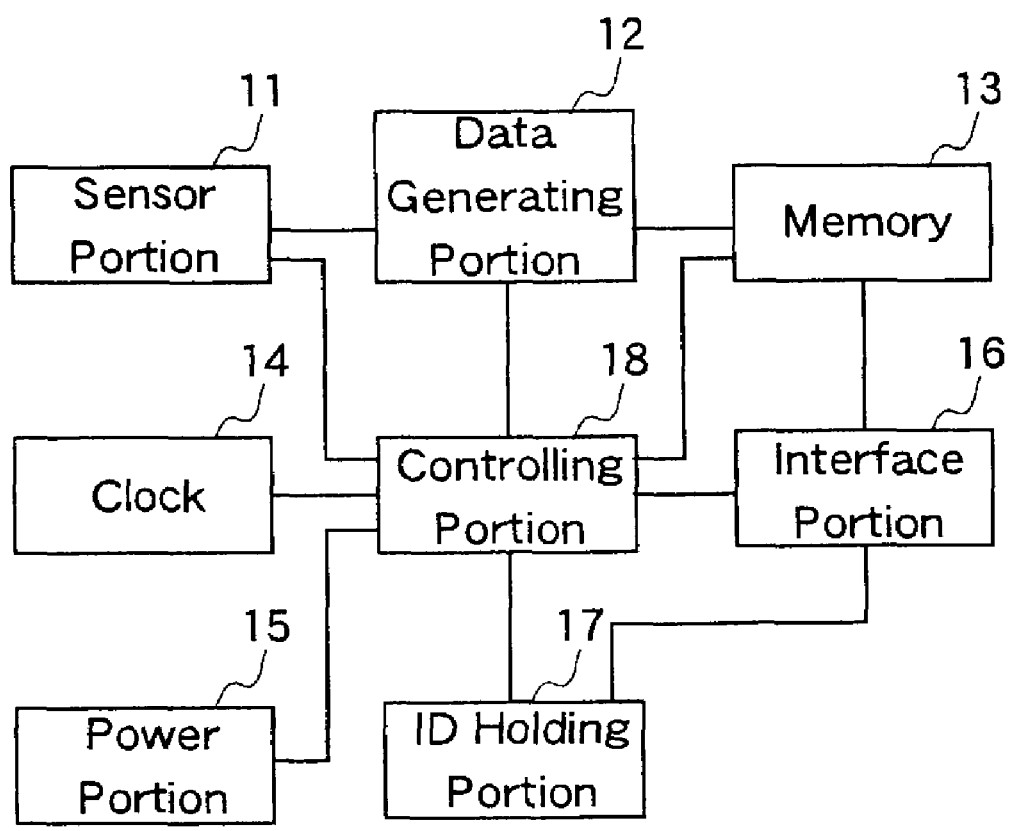
FIG. 2 is a block diagram showing a configuration of a personal measuring instrument contained in the measurement data processing system.

First, the configuration of the personal measuring instrument 1 will be described. FIG. 2 is a block diagram showing an internal configuration of the personal measuring instrument 1. The personal measuring instrument 1 includes a sensor portion 11, a data generating portion 12, a memory 13, a clock 14, a power portion 15, an interface portion 16, an ID holding portion 17 and a controlling portion 18.

The sensor portion 11 has a sensor according to an intended use of the personal measuring instrument 1. In other words, the personal measuring instrument 1, by nature, is constructed by specifying data to be dealt with. For example, if it is used as an electrocardiograph, the sensor portion 11 is provided with electrodes that are brought into contact with a patient's chest or limb and measures an action potential. Alternatively, if the personal measuring instrument 1 is used as a sphygmomanometer, the sensor portion 11 is provided with a pressure sensor. If the personal measuring instrument 1 is used as a blood sugar level meter, the sensor portion 11 is provided with a sensor for measuring a blood sugar level electrically or optically from a test paper to which a slight amount of blood taken from a fingertip of a patient is attached. It is needless to say that the use of the personal measuring instrument 1 is not limited to the electrocardiograph, the sphygmomanometer and the blood sugar level meter mentioned above.

The data generating portion 12 converts information obtained by the sensor portion 11 into data having a format storable in the personal measuring instrument 1, and assigns data-measurement date and time information obtained from the clock 14 to these data, which are then stored in the memory 13. The power portion 15 includes a battery, so that the personal measuring instrument 1 can be used without being connected to an AC power source.

The interface portion 16 transmits/receives data and various control signals to/from the computer 2 via the cable 3 according to a predetermined communication protocol. The ID holding portion 17 holds an ID number, which is assigned specifically to each personal measuring instrument 1. The controlling portion 18 controls an entire operation of the personal measuring instrument 1.

Next, the configuration of the computer 2 will be described. The computer 2 is constituted by known hardware such as a display, a hard disk, a CPU and a memory, and software for reading out and processing data from the personal measuring instrument 1 (in the following, referred to as a data processing program) is installed therein.

Figure 3:
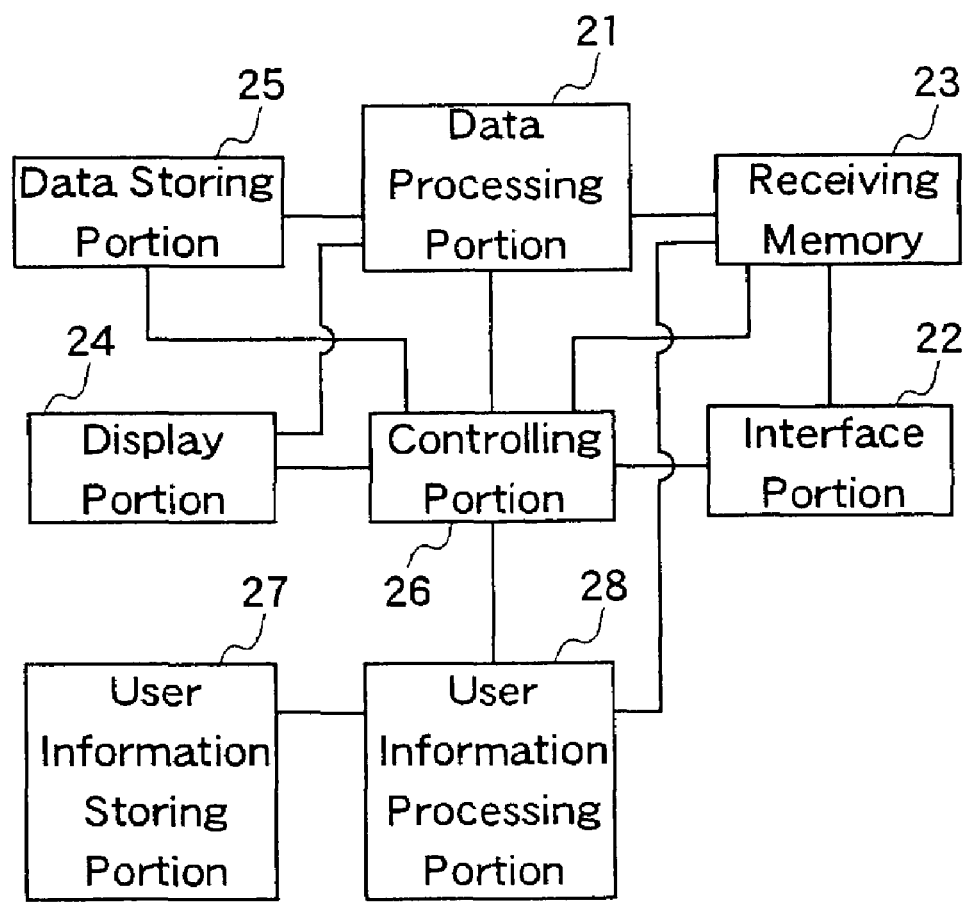
FIG. 3 is a block diagram showing a functional block of a computer contained in the measurement data processing system.

FIG. 3 illustrates a functional block of the computer 2 realized by a combination of these hardware and software. The computer 2 has a data processing portion 21, an interface portion 22, a receiving memory 23, a display portion 24, a data storing portion 25, a controlling portion 26, a user information storing portion 27 and a user information processing portion 28.

The data processing portion 21 receives data read out from the personal measuring instrument 1 and performs various processes such as data editing, statistical processing, for example calculation of a mean value, data analysis, data format conversion or graph making. It may be possible to preset which kinds of processings are performed or to select them after reading in the data from the personal measuring instrument 1.

The interface portion 22 transmits/receives data and various control signals to/from the personal measuring instrument 1 via the cable 3 according to a predetermined communication protocol. The receiving memory 23 functions as a buffer for retaining temporarily the data received from the personal measuring instrument 1. The display portion 24 displays on the display 2a the results of processing in the data processing portion 21. The data storing portion 25 stores the data read out from the personal measuring instrument 1 and various data regarding a system setting. The user information storing portion 27 stores, in association with an ID number assigned to each personal measuring instrument 1, user information such as a name, a gender and an age of the patient (user) who has this personal measuring instrument 1. In order to implement the data storing portion 25 and the user information storing portion 27 as hardware, they are not necessarily incorporated in the computer 2, but also can be realized as an external device of the computer 2. The controlling portion 26 controls an entire operation of the computer 2.

Further, the computer 2 has, in its interface portion 22, a port to be connected with the cable 3. Thus, one end of the cable 3 has a terminal shape adapted to the port of the computer 2, while the other end has a terminal shape adapted to the interface portion 16 of the personal measuring instrument 1.

Since a computer generally has a plurality of external interfaces, software for processing data inputted from the external interfaces has to recognize input paths of these data. In other words, when the computer 2 has a plurality of ports, the data processing program of the present embodiment also has to be set so that the port connected with the cable 3 is recognized as a source of the inputted data.

After such a setting is made as an initial setting at the time of installing the data processing program and connecting the cable 3, the content of setting is stored in a nonvolatile memory (for example, the data storing portion 25) of the computer 2. Consequently, once the initial setting is made, it is unnecessary to make the port setting again unless a port to be connected with the cable 3 is changed or the data processing program is reinstalled.

Figure 4:
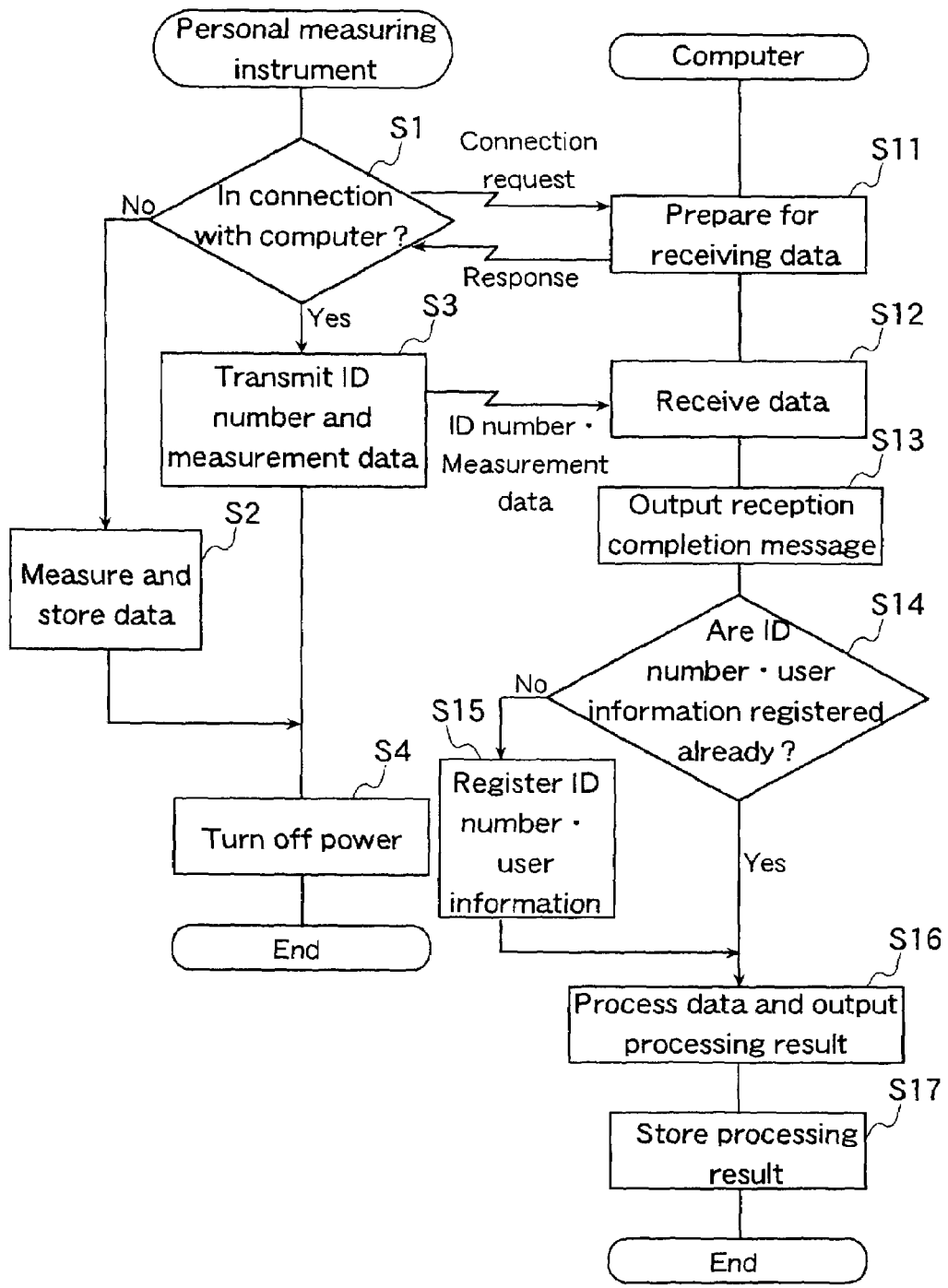
FIG. 4 is a flowchart showing operation sequences of the personal measuring instrument and the computer.

The following is an explanation of an operation of the data processing system. FIG. 4 is a flowchart showing operation sequences of the personal measuring instrument 1 and the computer 2.

When the power is turned on by pressing the power switch 1a, the controlling portion 18 of the personal measuring instrument 1 judges whether the personal measuring instrument 1 is connected to the computer 2 (Step S1), and operates in a data measuring mode if it is not connected (Step S2) or in a data transmitting mode if it is connected (Step S3).

In Step S1, the judgment whether the personal measuring instrument 1 is connected to the computer 2 is made as follows. When the power is turned on, the controlling portion 18 instructs the interface portion 16 to transmit to the computer 2 a connection request signal in accordance with a predetermined communication protocol. If no response to this connection request signal returns from the computer 2 after a predetermined time elapses, the interface portion 16 transmits another connection request signal. If no response returns from the computer 2 even after a predetermined number of times of transmitting the connection request signal and waiting for the response, the controlling portion 18 judges that the personal measuring instrument 1 is not connected to the computer 2.

When the personal measuring instrument 1 is judged not to be connected to the computer 2 in Step S1 and an operation mode is set to be the data measuring mode, the personal measuring instrument 1 converts the information obtained by the sensor portion 11 into a predetermined data format in the data generating portion 12 and stores the data in the memory 13 together with the measured date and time information (obtained from the clock 14), under the control of the controlling portion 18 (Step S2). Thereafter, by turning off the power (Step S4), the operation in the data measuring mode ends.

On the other hand, when the personal measuring instrument 1 is judged to be connected to the computer 2 in Step S1 and an operation mode is set to be the data transmitting mode, the personal measuring instrument 1 transmits the data stored in the memory 13 to the computer 2, under the control of the controlling portion 18 (Step S3).

In this embodiment, the cable 3 is connected in advance to a predetermined port of the computer 2, a data processing program is activated on the computer 2, and the setting already is made so that the data processing program recognizes the port with which the cable 3 is in connection as a source of the inputted data.

As described above, after returning a predetermined response to the connection request signal received from the personal measuring instrument 1, the interface portion 22 of the computer 2 prepares for receiving data, and when it is ready, sends out a predetermined data request signal to the personal measuring instrument 1 (Step S11).

When the personal measuring instrument 1 receives the data request signal, it sequentially reads out and transmits the ID number stored in the ID holding portion 17 and the data stored in the memory 13 to the computer 2 via the interface portion 16 and the cable 3. When the transmission of the ID number and the data stored in the memory 13 ends, the personal measuring instrument 1 transmits a data ending signal.

On the other hand, the computer 2 receives the data transmitted from the personal measuring instrument 1 via the cable 3 (Step S12). The received data are retained temporarily in the receiving memory 23. When the computer 2 receives the data ending signal from the personal measuring instrument 1, it ends the data reception, and the display portion 24 outputs to the display 2a a message for notifying the user that the reception is completed and instructing him/her to disconnect the personal measuring instrument 1 from the cable 3 (a reception completion message) (Step S13). The personal measuring instrument 1 disconnected from the cable 3 ends the operation in the data transmitting mode by turning off the power (Step S4).

Next, the controlling portion 26 of the computer 2 instructs the user information processing portion 28 to fetch from the receiving memory 23 the ID number received from the personal measuring instrument 1 and check whether this ID number already is registered together with the user information in the user information storing portion 27 (Step S14). If not, the display portion 24 shows a registration screen for the user information on the display 2a and allows the user to input the user information such as his/her name. The inputted user information is registered in the user information storing portion 27 in association with the above-mentioned ID number (Step S15).

Subsequently, the data processing portion 21 fetches and processes the data from the receiving memory 23, sends the results of processing to the display portion 24, and allows the results to be displayed on the display 2a of the computer 2 and to be printed out by the printer 4 (Step S16). At this time, the display portion 24 displays an ending confirmation message on the display 2a. When the user inputs a response to this message, the controlling portion 26 stores the results processed by the data processing portion 21 into the data storing portion 25 of the computer 2 (Step S17) and then ends the operation.

As described above, according to this data processing system, the user simply connects the personal measuring instrument 1 to the cable 3 and turns on the power by pressing the power switch 1a, whereby the measurement data automatically is transmitted to the computer 2 and the results of processing are printed out by the printer 4. In this manner, even a patient who is unfamiliar with a computer operation can obtain a necessary processing result easily. Also, simply by starting up the computer 2 and keeping the data processing program activated, the medical facility can collect data sequentially from a plurality of the personal measuring instruments 1 and obtain processing results, which achieves labor savings.

Further, the above description has been directed to an example of starting to fetch the measurement data from the personal measuring instrument 1 when triggered by turning on the power of the personal measuring instrument 1. However, in the case where this personal measuring instrument 1 is connected to the computer 2 after the power of the personal measuring instrument 1 is turned on, it also may be possible to start fetching the measurement data when triggered by connecting the personal measuring instrument 1 and the computer 2.

Also, the connection of the personal measuring instrument 1 and the computer 2 is not limited to wired connection such as the connection via the cable 3 but may be achieved by wireless communication by infrared rays or radio waves. Furthermore, the connection of the personal measuring instrument 1 and the computer 2 is not limited to direct connection but may be made via a public communication network such as a telephone network. In this case, the personal measuring instrument 1 and the computer 2 are connected to the public communication network via a (built-in or external) modem. This allows the user of the personal measuring instrument 1 to transmit measurement data to the computer 2 located in a medical facility via the telephone network from a remote location without visiting the medical facility.

In this case, the computer 2 automatically executes a series of operations from fetching the data to outputting the results of processing when triggered by the connection of the personal measuring instrument 1 via the public communication network, and then outputs the results to a facsimile receiver located in a house of the user of the personal measuring instrument 1.

In other words, once the telephone number of the facsimile receiver at home is registered in the user information storing portion 27 of the computer 2, the computer 2 outputs the results of processing to the facsimile receiver via the modem and the telephone network. This allows the user of the personal measuring instrument 1 to obtain the results of processing the measurement data at home.

The results of processing are not necessarily output to the facsimile receiver but may be output to a personal computer or a portable terminal such as a cellular phone of the user.

Moreover, the data measuring device according to the present invention is not limited to the use in medical facilities but may be applied suitably to any field as long as it is a data measuring device for measuring and storing data. Also, the measurement data processing system according to the present invention is not limited to the use in medical facilities but may be applied suitably to any field as long as it is a system constituted by a combination of a data measuring device for measuring and storing data and a data processing device for fetching and processing the data from the data measuring device.

INDUSTRIAL APPLICABILITY

As described above, in accordance with the present invention, it is possible to provide a measurement data processing system that can transmit measurement data to a computer and obtain easily the results processed by the computer, simply by connecting a personal measuring instrument to a cable and turning on the power.

The invention claimed is:

1. A measurement data processing system comprising:
a data measuring device; and
a data processing device;
wherein the data measuring device measures and stores data into an internal memory in a state disconnected from the data processing device,
the data processing device fetches and processes the data from the data measuring device and then outputs a result of the processing in a state connected to the data measuring device via wired or wireless communication,
the data measuring device transmits to the data processing device a signal for judging whether the data measuring device is connected to the data processing device when the power is turned on, sets an operation mode to be an automatic data transmitting mode if a connection confirmation response to the signal is returned from the data processing device, and sets the operation mode to be a data measuring mode if the connection confirmation response is not returned, and
after returning the connection confirmation response to the signal from the data measuring device, the data processing device starts fetching the data from the data measuring device.

2. A measurement data processing system comprising:
a data measuring device; and
a data processing device;
wherein the data measuring device measures and stores data into an internal memory in a state disconnected from the data processing device,
the data processing device fetches and processes the data from the data measuring device and then outputs a result of the processing in a state connected to the data measuring device via wired or wireless communication,
the data measuring device transmits to the data processing device a signal for judging whether the data measuring device is connected to the data processing device, sets an operation mode to be an automatic data transmitting mode if a connection confirmation response to the signal is returned from the data processing device, and sets the operation mode to be a data measuring mode if the connection confirmation response is not returned, and
after returning the connection confirmation response to the signal from the data measuring device, the data processing device starts fetching the data from the data measuring device.

3. The measurement data processing system according to claim 2, wherein the data measuring device is connected to the data processing device via a public communication network.

4. The measurement data processing system according to claim 3, wherein the result of processing the data is outputted from the data processing device to a receiver of a user of the data measuring device.

5. A data measuring device for measuring and storing bioiogical data of a user into an internal memory in an off-line state and transmitting the biological data to a data processing device in a state connected to the data processing device via wired or wireless communication, the data measuring device comprising:
an interface portion for transmitting to the data processing device a signal for judging whether the data measuring device is connected to the data processing device when a power is turned on by a presence or an absence of a connection confirmation response to the signal returned from the data processing device; and
an operation controlling portion for setting an operation mode to be an automatic data transmitting mode for transmitting the biological data stored in the internal memory to the data processing device if the data measuring device is connected to the data processing device, and setting the operation mode to be a data measuring mode for measuring the biological data if the data measuring device is not connected to the data processing device.

6. A data measuring device for measuring and storing biological data of a user into an internal memory in an off-line state and transmitting the biological data to a data processing device in a state connected to the data processing device via wired or wireless communication, the data measuring device comprising:
an interface portion for transmitting to the data processing device a signal for judging whether the data measuring device is connected to the data processing device by a presence or an absence of a connection confirmation response to the signal returned from the data processing device; and
an operation controlling portion for setting an operation mode to be an automatic data transmitting mode for transmitting the biological data stored in the internal memory to the data processing device if the data measuring device is connected to the data processing device, and setting the operation mode to be a data measuring mode for measuring the biological data if the data measuring device is not connected to the data processing device.

7. A data processing device for, when a data measuring device that has measured and stored data in an off-line state is connected to the data processing device via wired or wireless communication, receiving and processing the data from the data measuring device, the data processing device comprising:
an interface portion that detects that a power of the data measuring device is turned on by a signal transmitted by the data measuring device to the data processing device for judging whether the data measuring device is connected to the data processing device after the data measuring device is connected to the data processing device via the wired or wireless communication; and a data processing portion that, when the interface portion detects that the power of the data measuring device is tuned on, automatically starts fetching the data from the data measuring device after returning a connection confirmation response to the signal to the data measuring device.

8. A data processing device for, when a data measuring device that has measured and stored data in an off-line state is connected to the data processing device via wired or wireless communication, receiving and processing the data from the data measuring device, the data processing device comprising:

an interface portion that detects that the data measuring device is connected to the data processing device via the wired or wireless communication by a signal transmitted by the data measuring device to the data processing device for judging whether the data measuring device is connected to the data processing device; and a data processing portion that, when the interface portion detects that the data measuring device is connected to the data processing device, automatically starts fetching the data from the data measuring device after returning a connection confirmation response to the signal to the data measuring device.

9. A computer-readable recording medium storing a program for allowing a computer to execute operations of:

after a data measuring device that has measured and stored data in an off-line state is connected to the computer via wired or wireless communication, detecting that a power of the data measuring device is turned on by a signal transmitted by the data measuring device to the computer for judging whether the data measuring device is connected to the computer;

when detection is made that the power of the data measuring device is turned on, automatically starting to fetch the data from the data measuring device after returning a connection confirmation response to the signal to the data measuring device;

processing the data that has been fetched; and outputting a result of the processing.

10. A computer-readable recording medium storing a program for allowing a computer to execute operations of:

detecting that the data measuring device that has measured and stored data in an off-line state is connected to the computer via wired or wireless communication by a signal transmitted by the data measuring device to the computer for judging whether the data measuring device is connected to the computer;

when detection is made that the data measuring device is connected to the computer, automatically starting fetching the data from the data measuring device after returning a connection confirmation response to the signal to the data measuring device;

processing the data that has been fetched; and outputting a result of the processing.

* * * * *